United States Patent
Lin

(10) Patent No.: US 7,172,416 B2
(45) Date of Patent: Feb. 6, 2007

(54) SCREW DEVICE FOR ORTHODONTIC TREATMENT

(76) Inventor: Cheng-Yi Lin, No. 190-1, Sec. 1 WenHua Rd., Banchao, Taipei County (TW)

( * ) Notice: Subject to any disclaimer, the term of this patent is extended or adjusted under 35 U.S.C. 154(b) by 67 days.

(21) Appl. No.: 10/885,580

(22) Filed: Jul. 8, 2004

(65) Prior Publication Data

US 2005/0130093 A1    Jun. 16, 2005

Related U.S. Application Data

(63) Continuation-in-part of application No. 10/732,292, filed on Dec. 11, 2003.

(51) Int. Cl.
*A61C 3/00* (2006.01)
*A61C 8/00* (2006.01)
(52) U.S. Cl. .......................... 433/18; 433/174
(58) Field of Classification Search .............. 433/18, 433/172, 173, 174, 175, 176
See application file for complete search history.

(56) References Cited

U.S. PATENT DOCUMENTS 5,306,142 A * 4/1994 Richards ..................... 433/22
5,588,838 A * 12/1996 Hansson et al. ............ 433/173
5,697,779 A * 12/1997 Sachdeva et al. ............. 433/2
6,312,259 B1 * 11/2001 Kvarnstrom et al. ........ 433/173
2002/0182560 A1 * 12/2002 Park et al. ..................... 433/18

* cited by examiner

Primary Examiner—Cary E. O'Connor
(74) Attorney, Agent, or Firm—Troxell Law Office PLLC

(57) ABSTRACT

A screw device for orthodontic treatment comprises a screw-body part, a platform part integrally formed with the screw-body part, and a head part. The head part is detachable from and exposed outside the screw-body part and is operatable to hook a spring (or rubber band) for orthodontic treatment. Since the head part is detachable, various types of head parts can be chosen to attach on the same platform part and screw-body part for performing different orthodontic treatments. Cost to manufacture the screw device is lower, and flexibility and convenience to use the screw device are higher. The threads of the screw-body part are divided into at least a first thread portion located near to the platform part and a second thread portion located away from the platform part. The threads of the first thread portion are designed to have relatively narrower width and smaller pitch, while the threads of the second thread portion have wider width and larger pitch.

10 Claims, 13 Drawing Sheets

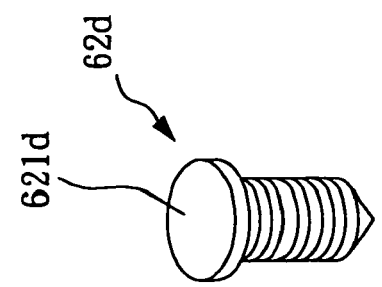
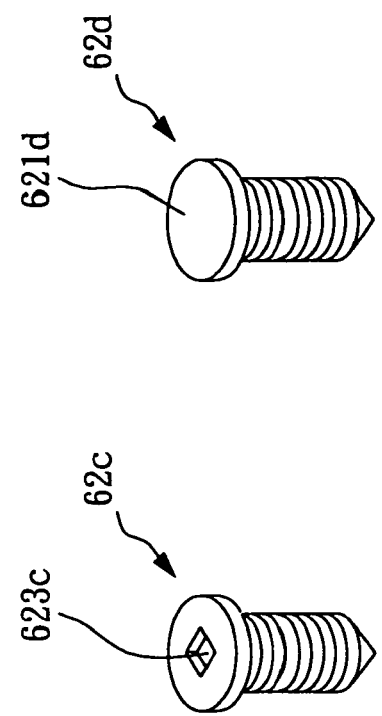
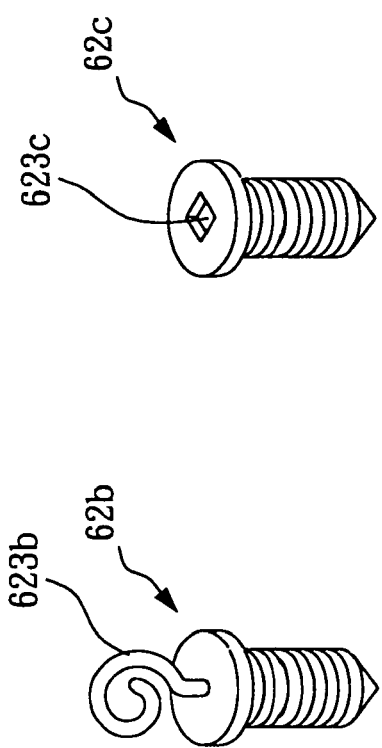
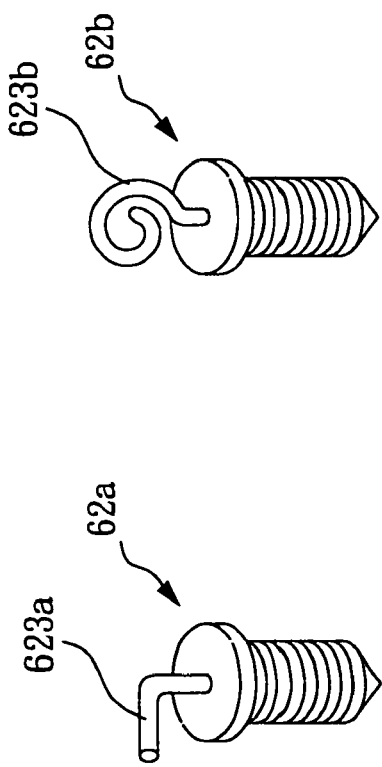
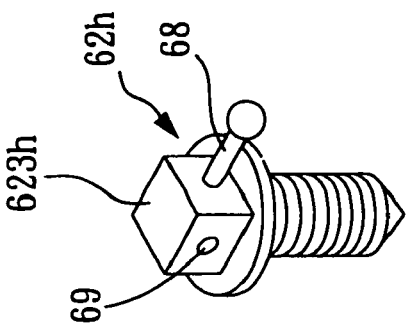
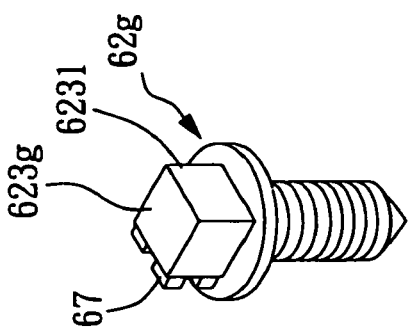
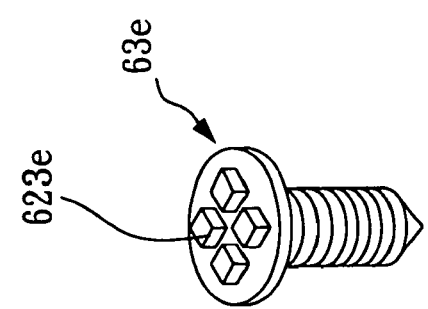

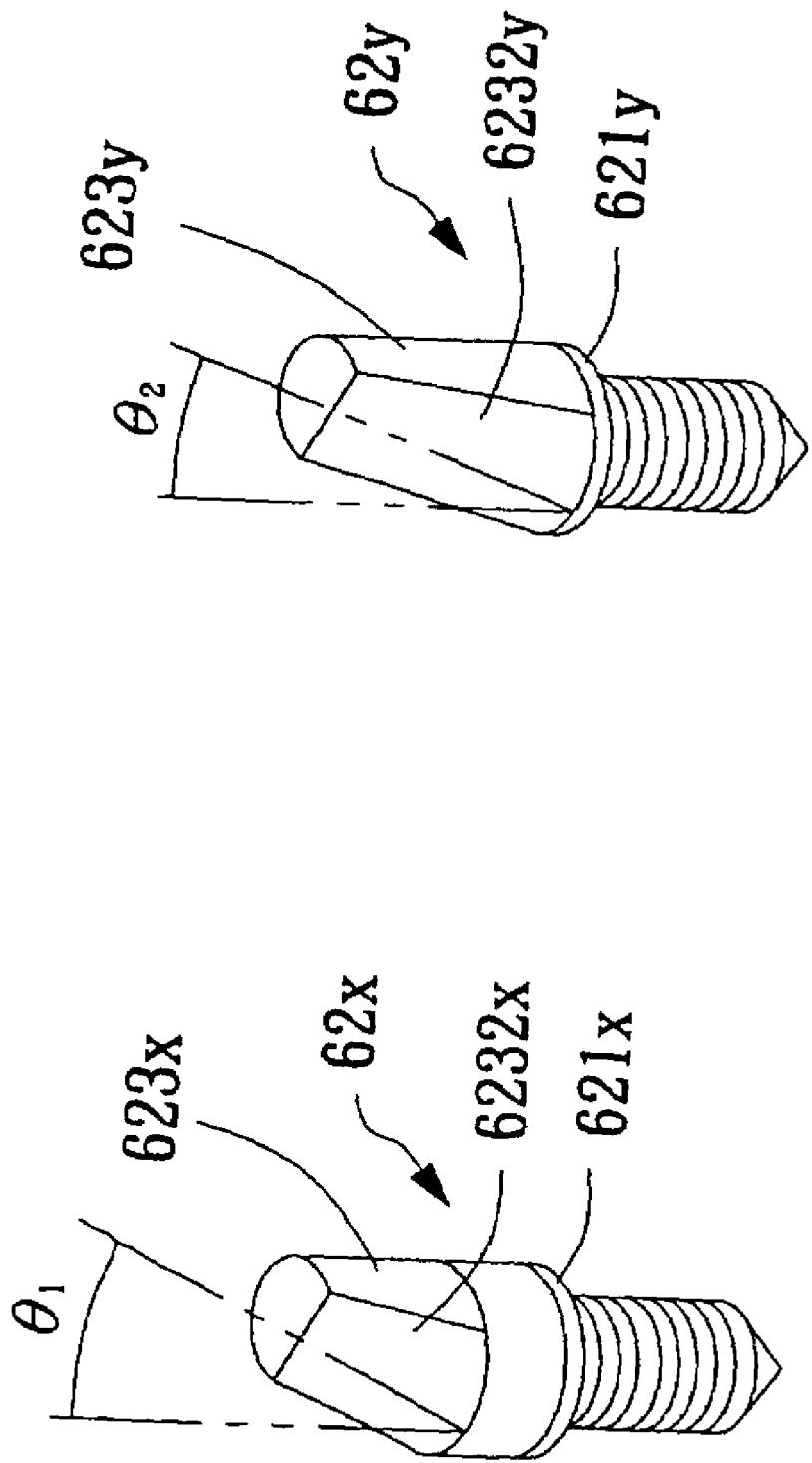

SCREW DEVICE FOR ORTHODONTIC TREATMENT

This application is a continue-in-part (CIP) application of U.S. patent application Ser. No. 10/732,292 filing date Dec. 11, 2003 which is now pending.

FIELD OF THE INVENTION

The invention relates to a screw device for orthodontic treatment, especially to a screw device that may be arranged in the maxilla (or mandible) and is capable of positioning the spring used for orthodontic treatment and accommodating the orthodontic archwire.

BACKGROUND OF THE INVENTION

As shown in FIG. 1, in a conventional orthodontic treatment process, after part of the maxilla (or mandible) 10 is cut off or a tooth 12 is pulled out (usually not the incisor), the tooth 12 or the maxilla (or mandible) 10 is pulled and dragged by an orthodontic archwire 13 after the operation for helping the maxilla (or mandible) 10 to heal over or correcting the position of the tooth 12. In order to maintain the position of the orthodontic archwire 13 relative to the tooth 12, it is usually to apply several orthodontic brackets 14 adhered onto the tooth 12, and each orthodontic bracket 14 is arranged with slot 141 for providing an accommodation for the orthodontic archwire 13. The width and the depth of the slot 141 must be slightly larger than the diameter of the orthodontic archwire 13 such that, not only may the orthodontic archwire 13 be appropriately glided along the extensive direction of the slot 141, but also may the orthodontic archwire 13 be kept from being dropped out of the slot 141.

As known in the prior arts, in order to provide a pulling-and-dragging force to the orthodontic archwire 13, a screw 20 is screwed on a maxilla (or mandible) 10 at the adjacency of a molar 121, then a spring 15 or rubber band is further connected between the screw 20 and the end of the orthodontic archwire 13 for providing an appropriate pulling-and-dragging force. Since the end of this kind of spring 15 used specially for orthodontic treatment in current market is all arranged with a hook ring 151 so, for the connection between the spring 15 and the end of the orthodontic archwire 13, the end of the orthodontic archwire 13 just may be bent into a hook structure 131, then it can be easy to fit the hook ring 151 of the spring 15 into the hook structure 131 of the end of the orthodontic archwire 13, such that both connection is completed. Relatively, the connection between the spring 15 and the screw 20 is more difficult relatively.

U.S. Pat. No. 4,988,292 discloses an abutment for orthodontic anchorage to a dental implant fixture. It comprises an endosseous implant fixture which is fixed in the lower jaw at the site of a missing molar for supporting an abutment for orthodontic anchorage. The abutment and the fixture are connected by a bolt in a detachable manner. However, the abutment of U.S. Pat. No. 4,988,292 does not provide the function of spring hooking. Even if someone tries to hook the spring on the abutment, the spring will be prone to impinge the gingival as previously illustrated. In addition, the fixture is prone to loose since it has identical outer threads and identical outer diameter throughout the entire fixture.

U.S. Pat. No. 5,836,768 discloses a fastening device for fixing orthodontic apparatuses on a dental implant. It comprises an implant which is fixed in the jaw bone, an anchoring screw screwed within an axially arranged threaded bore in the implant, and an occlusal screw located inside the threaded bore and engaged with the anchoring screw. None part of the occlusal screw nor anchoring screw is exposed outside the implant, such that they cannot be used for spring hooking. Even if the spring can be tied (not hook) on a bracket of U.S. Pat. No. 5,836,768, the spring will be prone to impinge the gingival. In addition, the implant is prone to loose since it has identical outer threads and identical outer diameter.

U.S. Pat. No. 5,921,774 discloses a supporting body for use in orthodontic appliance. It comprises a supporting body to be fixed in the jaw bone, an abutment formed with an arm at a side surface thereof, and a male screw for screwing and fixing the abutment onto the top of the supporting body. Since the screw is an independent element and is screwed from a top side of the abutment, therefore the arm can only be form at the side surface of the abutment, and thus the application and flexibility thereof are limited. In addition, the device disclosed by U.S. Pat. No. 5,921,774 comprises at least three elements (e.g., supporting body, abutment and male screw). Not only the cost to manufacture is higher, but also is more complex to use. Moreover, the supporting body is prone to loose since it has identical outer threads (or no threads at all) and identical outer diameter throughout the entire supporting body.

Other prior art, such like U.S. Pat. No. 6,241,516, U.S. Pat. No. 5,071,345, and US Pub. No. 2002/0127510. None of them has been disclosed a screw device which comprises a screw-body part, a platform part and a head part which is detachable from and exposed outside the platform part (or screw-body part) and is operatable to hook the spring for orthodontic treatment.

As known from above description, the prior arts that are used for orthodontic treatment currently still have many shortcomings to be further improved urgently.

Publication No. U.S. 2003/00224315 A1 and Publication No. U.S. 2003/0023182 A1 are two patent applications filed by the same inventor of the present invention, which disclosed some embodiments of improved screw devices for facilitating orthodontic treatments.

SUMMARY OF THE INVENTION

The main objective of the invention is to provide an improvement for a screw device for orthodontic treatment. The screw device in accordance with the present invention comprises a screw-body part, a platform part and a head part. The head part is detachable from and exposed outside the platform part and is operatable to hook the spring for orthodontic treatment. The threads of the screw-body part are divided into at least a first thread portion located near to the platform part and a second thread portion located away from the platform part. The threads of the first thread portion are designed to have relatively narrower width and smaller pitch, while the threads of the second thread portion have wider width and larger pitch.

For further understanding the objects, the characteristics, and the functions of the structures of the present invention, a detailed description matched with corresponding drawings are presented as follows.

BRIEF DESCRIPTION OF THE DRAWINGS

FIGS. 4A~4J are some preferred embodiments of the head parts 62a~62h, 62x and 62y which can be fixed to the platform part 63 and screw-body part 61 as shown in FIG. 2 of the present invention.

DETAILED DESCRIPTION OF THE INVENTION

Figure 1:
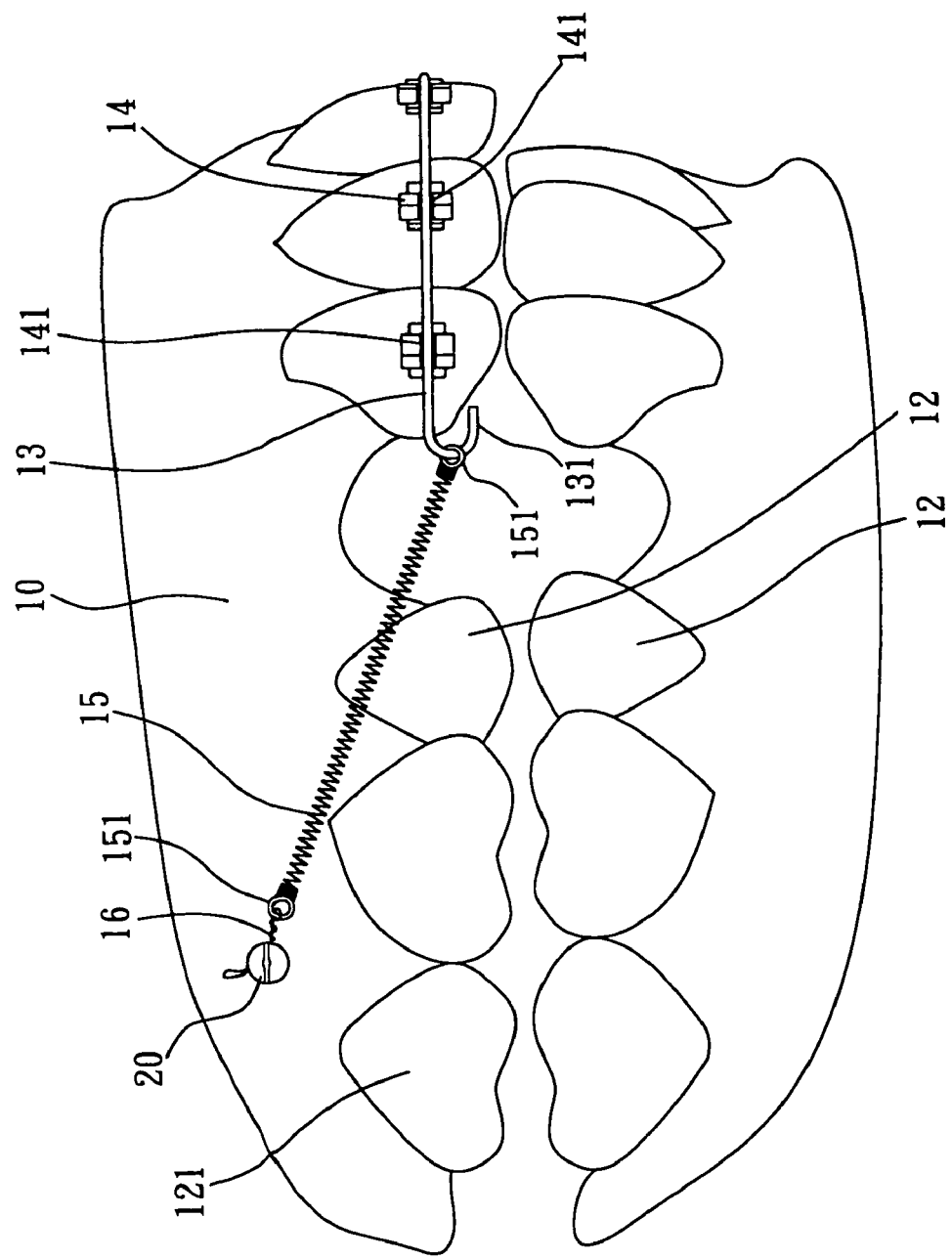
FIG. 1 is an embodiment illustration for a screw device, according to the prior arts, arranged in the mouth for orthodontic treatment.

The elements described thereinafter, such as: maxilla (or mandible) 10, gingiva 11, tooth 12, orthodontic archwire 13, orthodontic bracket 14, and spring 15 (or rubber band) for orthodontic treatment etc., and their relative position arranged in the mouth are all similar to the prior arts shown in FIG. 1 and they are not the technical characteristics of the invention, so they will be given same element names and referential numbers and their detailed composition, arrangement position, and function are not described herein repetitiously. One thing is worth mentioning: although the embodiment of the prior arts shown in FIG. 1 only depicts an embodiment that a correction device is arranged on the outside of the upper jaw, however, it may also be arranged on the outside or inside surface of maxilla (or mandible).

Figure 3:
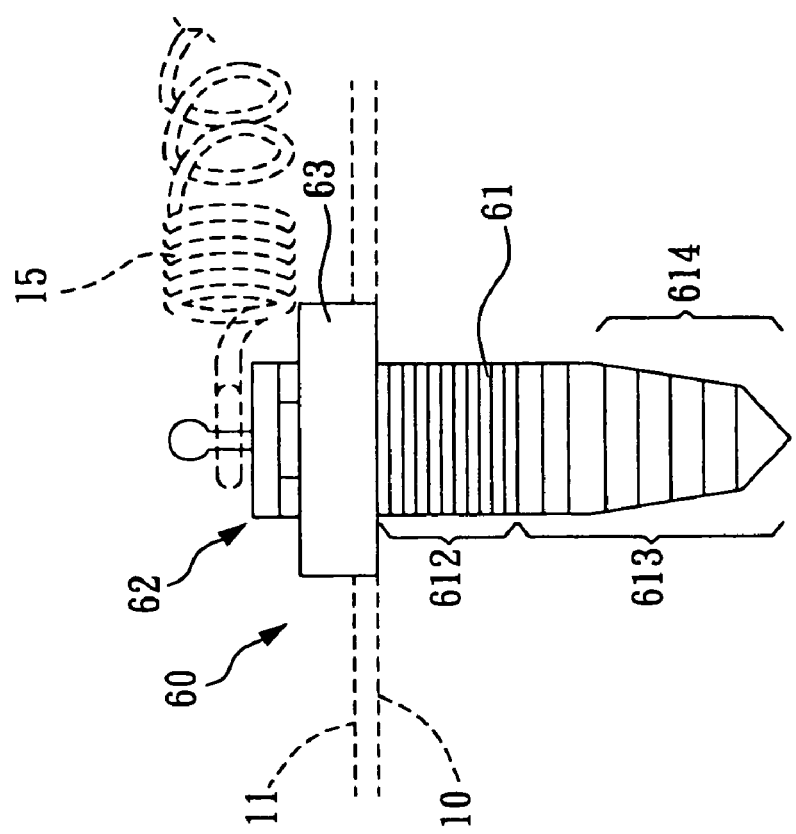
FIG. 3 is a front view of the first preferred embodiment shown in FIG. 2, wherein the head part 62 is attached onto the platform part 63 of the screw device 60.
Figure 2:
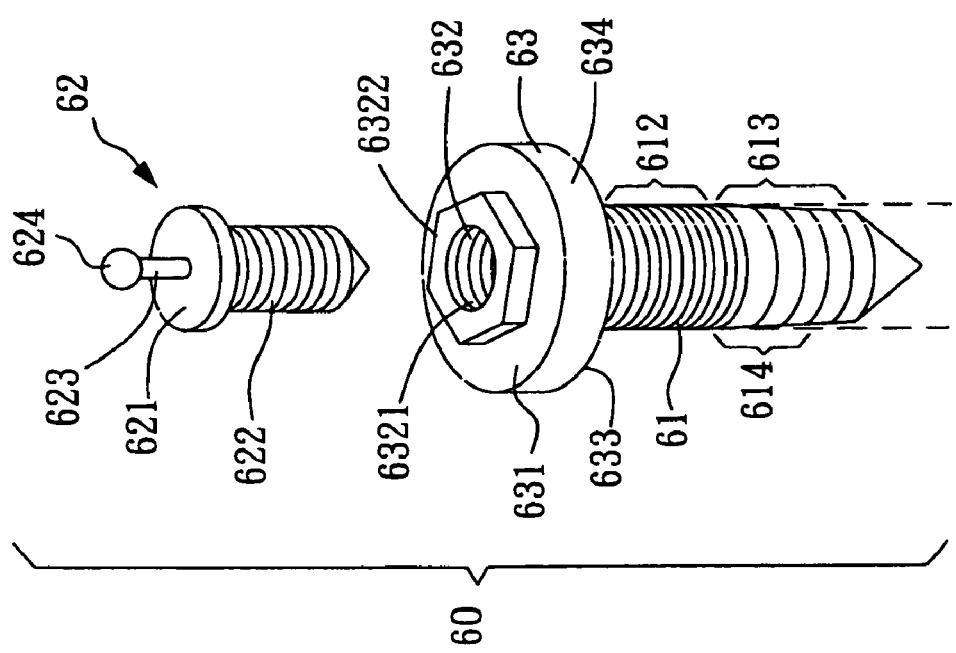
FIG. 2 is a perspective view of the first preferred embodiment of the screw device for orthodontic treatment according to the present invention.

Please refer to FIG. 2 and FIG. 3. FIG. 2 is the first preferred embodiment for the screw device according to the invention for orthodontic treatment. FIG. 3 is a schematic drawing showing the screw device of FIG. 2 being fixed on the maxilla (or mandible) for orthodontic treatment.

As shown in FIG. 2 and FIG. 3, the fourteenth preferred embodiment of the screw device 60 in accordance with the present invention comprises: a screw-body part 61, a platform part 63 and a head part 62. The screw-body part 60 has a diameter with external threads extending a length. The platform part 63 is axially aligned and integrally formed with the screw-body part 61 to be a single element. The head part 62 is separately manufactured and is an independent element.

In this preferred embodiment, the external threads of the screw-body part 61 are slightly loosened at a portion 613 away from the platform part 63 and are relatively concentrated at another portion 612 near to the platform part 63. In addition, the screw-body part 61 is tapered at a section 614 away from the platform part 63. In one embodiment, the tapered section 614 of the screw-body part 61 has a tapering angle of around 2~10 degrees. By such arrangement, the user (for example, a dentist) will be easy to operate at the beginning when he/she starts screwing the screw device 60 into an object (for example, the maxilla or mandible of a patient). It is because the bottom tip (i.e., section 614) of the screw-body part 61 is narrower and the threads on that portion 613 are relatively loosened, such that the user does not need much effort/strength to screw it. When the user is about to screw the entire screw-body part 61 into the object, the gradually enlarged diameter and concentrated threads (at portion 612) of the screw-body part 61 will provide more tightened and secured fixing result. Of course, the user will need relatively more effort/strength to screw it when the top portion 612 of the screw-body part 61 entering the object. The other advantage for designing the screw-body part 61 with loosened threads and tapered end is that, since the maxilla/mandible of human includes a relatively fragile inner structure and a relatively hard and firm outer structure. The loosened threads and tapered end of the screw-body part 61 can prevent the fragile inner structure of the maxilla/mandible being damaged, while a firm fixing result can still be obtained when the screw-body part 61 is almost entirely screwed into the maxilla/mandible. In addition, the outer surface of the screw-body part 61 (e.g. surfaces of threads) can be roughened to increase friction between the screw-body part 61 and the object (e.g. the maxilla or mandible), such that the screw device 60 of the present invention can be fixed on the object even firmer. Methods for roughening the surfaces of threads include chemical etching and other conventional techniques. Conventional HA particles can also be applied on the surfaces of threads to improve the biointegration effect.

The platform part 63 further comprises a flat top plane 631, a first mating structure 632, a flat bottom plane 633 and an outer periphery 634. In this embodiment, the platform part 63 has a width larger than the width of the screw-body part 61 and the width of the head part 62. The outer periphery 634 is a smooth surface without threads thereon. The shape of the outer periphery 634 can be either round shaped as shown in FIG. 2 or polygon shaped (i.e., being a polygon from the top view thereof). The flat top plane 631 is perpendicular to the screw-body part 61. The first mating structure 632 is formed on the flat top plane 631 and comprises a screw hole 6321 and a nut contour 6322. The screw hole 6321 is for fixing the head part 62. The nut contour 6322 allows the user to use a tool to screw the screw-body part 61 into the object. The flat bottom plane 633 is adjacent to the top end of the screw-body part 61 and is perpendicular to the screw-body part 61, such that when the screw-body part 61 is entirely screwed into the object, the bottom plane 633 will contact a surface of the object (maxilla/mandible 10), as which shown in FIG. 3. As a result, not only the screw device can be fixed firmly, but also the gingiva 11 can recover rapidly and beautifully. Of course, it is also possible for a user (dentist) not to screw the entire screw-body part 61 into the object (maxilla/mandible 10). In this circumstance, there will be a gap between the bottom plane 633 and the object (maxilla/mandible 10). However, since the bottom plane 633 is a flat surface and the outer periphery 634 is a smooth surface, they can still help the gingiva 11 to recover well.

The head part 62 is detachable from the platform part 63 and further comprises a flat cap 621, a second mating structure 622 and an accessory member 623. The second mating structure 622 is formed on a bottom side of the flat cap 62. The second mating structure 622 is capable of engaging with the first mating structure 632 so as to fix the head part 62 onto the platform part 63. In this preferred embodiment, the second mating structure 622 is a screw. The accessory member 623 is formed on a top side of the flat cap 621 for assisting orthodontic treatment. The accessory member 623 is exposed outside of the platform part 63 when the second mating structure 622 engages with the first mating structure 632, such that operations of orthodontic treatment are possible to be performed on the accessory member 623. In the preferred embodiment, the accessory member 623 is formed as a rod-like neck with a uniform width. The neck (accessory member 623) is axially aligned with the screw-body part 61 and extends outwardly from the top side of the flat cap 621 at a first end thereof. The neck (accessory member 623) is configured to removably hook one end of the spring 15. A ball head 624 is located at the top end of the accessory member 623. The ball head 624 has a diameter larger than which of the neck so as to prevent the spring 15 from dropping. The reason why the rod-like neck is axially aligned with the screw-body part 61 and extends outwardly from the top side of the flat cap 621 is that, the thickness of the platform part 63 can act as a protector to prevent the spring 15 from damaging the tissues of the gingiva 11.

FIGS. 4A~4J are some preferred embodiments of the head parts 62a~62h, 62x and 62y which can be fixed to the platform part 63 and screw-body part 61 of the present invention. Because the head part 62 of the present invention is detachable and changeable, it is possible to design various types of head parts 62a~62h, 62x and 62y to mate with the same type of platform part 63 and screw-body part 61 so as to achieve different purposes of orthodontic treatments. Flexibility and convenience for using the screw device 60 are increased. In the mean time, only one type of platform part 63 and screw-body part 61 is needed to be manufactured, thus cost to make screw devices with different functions is decreased. As shown in FIG. 4A, the accessory member 623a of the head part 62a is formed as an L-shaped structure. In FIG. 4B, the accessory member 623b of the head part 62b is formed as a hook shaped structure. In FIG. 4C, the accessory member 623c of the head part 62c is a concave formed on the top surface of the head part 62c. The concave (623c) can be used to fill with adhesive to attach an additional component (not shown) for orthodontic treatment as required, for example, an orthodontic bracket or etc. In FIG. 4D, there is no accessory member being formed on the head part 62d, such that the top surface of the flat cap 621d is a plane. User (dentist) can attach an additional component on the top surface of the flat cap 621d if required. In FIG. 4E, the accessory member 623e of the head part 62e is an orthodontic bracket for accommodating an orthodontic archwire (not shown). In FIG. 4F, the accessory member 623f of the head part 62f is a rod-like neck as which shown in FIG. 2. However, the flat cap 621f of this embodiment is thicker and is formed with a rectangular through hole 66 for allowing an orthodontic archwire to pass therethrough. In FIG. 4G, the accessory member 623g of the head part 62g is a cubic having a plurality of flat side surfaces 6231. An additional component, such like an orthodontic bracket 67, can be adhered to one of the flat side surfaces 6231 to assist orthodontic treatment. In FIG. 4H, the accessory member 623h of the head part 62h is a cubic having a rod-like neck 68 formed on a side surface thereof for hooking a spring. The cubic is further formed with a round through hole 69 for allowing an orthodontic archwire to pass therethrough. In FIG. 4I, the accessory member 623x of the head part 62x has an inclined plane 6232x located on the flat cap 621x. There is an inclined angle $\theta_1$ between the axis of the second mating structure (e.g. the screw) and the inclined plane 6232x. Users (for example, orthodontic doctors) can attach additional component on the inclined plane 6232x for assisting orthodontic treatment. In a preferred embodiment, the inclined angle $\theta_1$ can be 30°, 45°, 60° or other angles. FIG. 4J shows yet another embodiment of the head part 62y in which the inclined plane 6232y of the accessory member 623y has an even smaller inclined angle $\theta_2$. The inclined angle $\theta_2$ is typically smaller than 30° in this embodiment. In addition, the flat cap 621y has a thickness smaller than which of the FIG. 4I.

Figure 5:
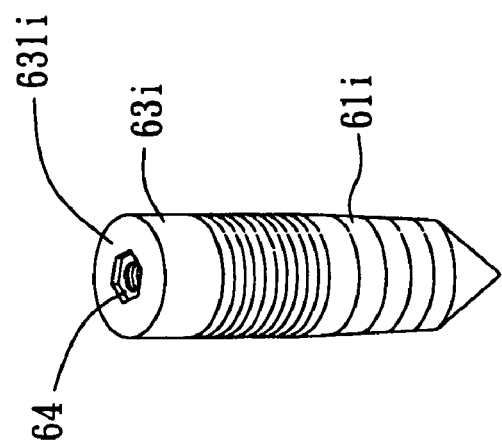
FIG. 5 is the second preferred embodiment of the screw-body part 61i and platform part 63i of the screw device according to the present invention.

FIG. 5 is the second preferred embodiment of the screw-body part 61i and platform part 63i in accordance with the present invention. In this embodiment, the platform part 63i has a diameter equal to which of the screw-body part 61i. In addition, the flat top plane 631i of the platform part 63i is formed with a nut-shaped bore 64 for allowing a tool, such like a driver, to mate therewith.

Figure 6:
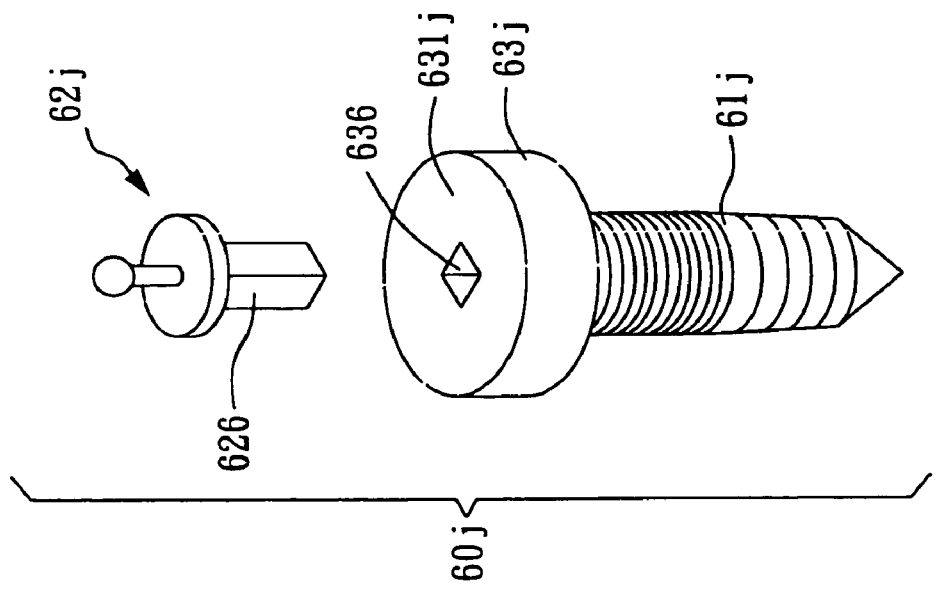
FIG. 6 is the third preferred embodiment of the screw device 60j according to the present invention.

FIG. 6 is the third preferred embodiment of the screw device 60j according to the present invention. In this embodiment, the first mating structure is a polygon shaped bore 636 formed on the flat top plane 631j of the platform part 63j. The polygon shaped bore 636 is aligned with the screw-body part 61j. In addition, the second mating structure of the head part 62j is a polygon shaped pillar 626 which can be plugged into and fixed firmly with the polygon shaped bore 636 by adhesive.

Figure 7:
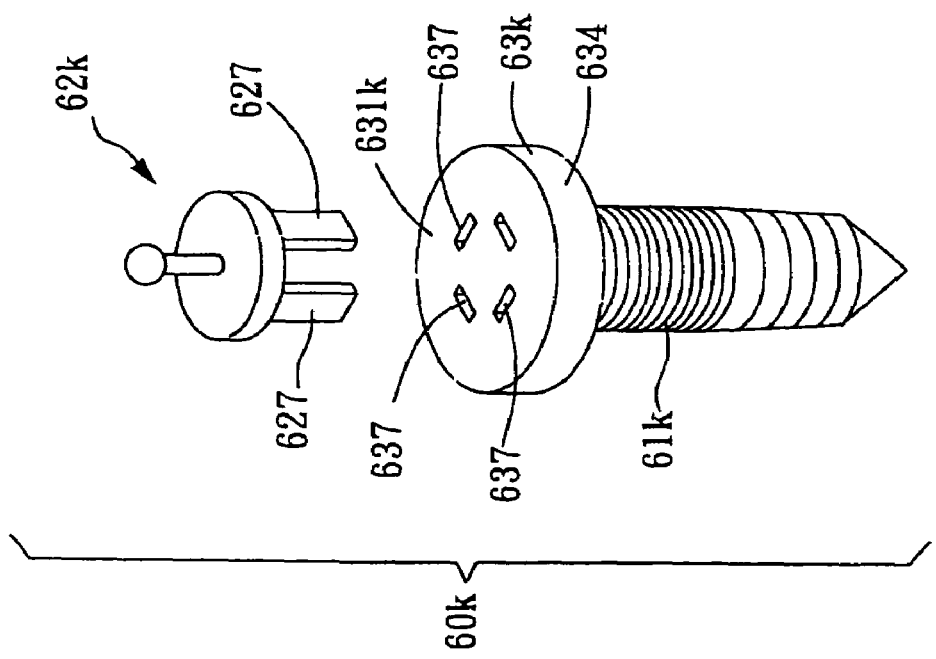
FIG. 7 is the fourth preferred embodiment of the screw device 60k according to the present invention.

FIG. 7 is the fourth preferred embodiment of the screw device 60k according to the present invention. In this embodiment, the first mating structure includes a plurality of sockets 637 formed on the flat top plane 631k of the platform part 63k. The second mating structure of the head part 62k is a plurality of plugs 627 which are so shaped and positioned that they can be plugged into and fixed firmly with the sockets 637 by adhesive.

Figure 8:
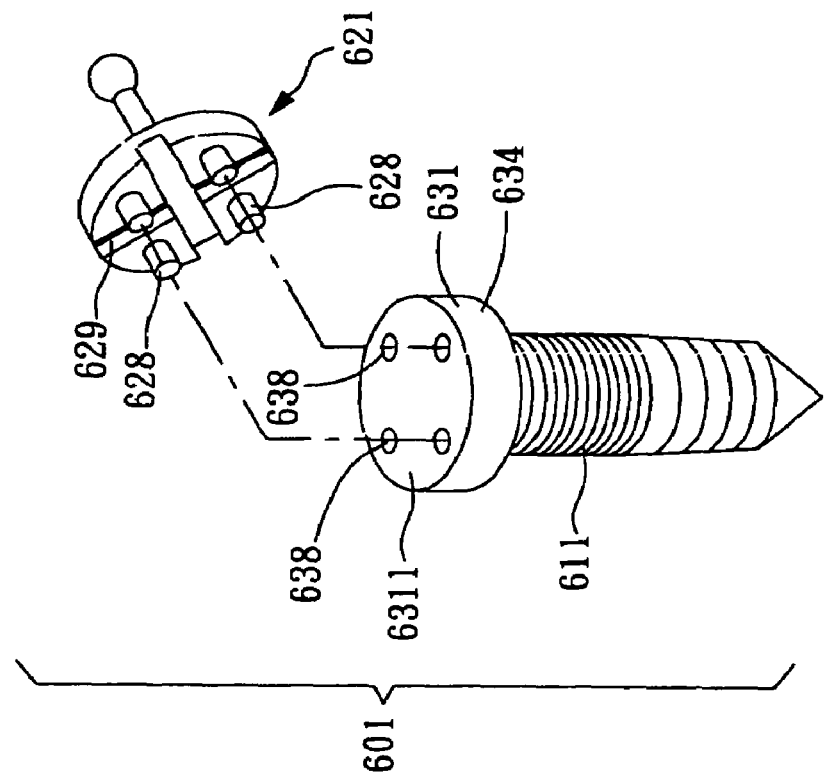
FIG. 8 is the fifth preferred embodiment of the screw device 60l according to the present invention.

FIG. 8 is the fifth preferred embodiment of the screw device 601 according to the present invention. In this embodiment, the first mating structure includes a plurality of pin holes 638 formed on the flat top plane 6311 of the platform part 631. The second mating structure of the head part 621 is a plurality of pins 628 which are so shaped and positioned that they can be plugged into and fixed firmly with the sockets 638 by adhesive. In addition, the head part 621 is formed with a crisscross-shaped rectangular groove 629 on a surface thereof facing the flat top plane 6311 of the platform part 631. Such that, when the head part 621 is fixed to the platform part 631, the crisscross-shaped rectangular groove 629 substantially becomes two rectangular through holes (intersecting with each other) for allowing the orthodontic archwire to pass therethrough.

Figure 9:
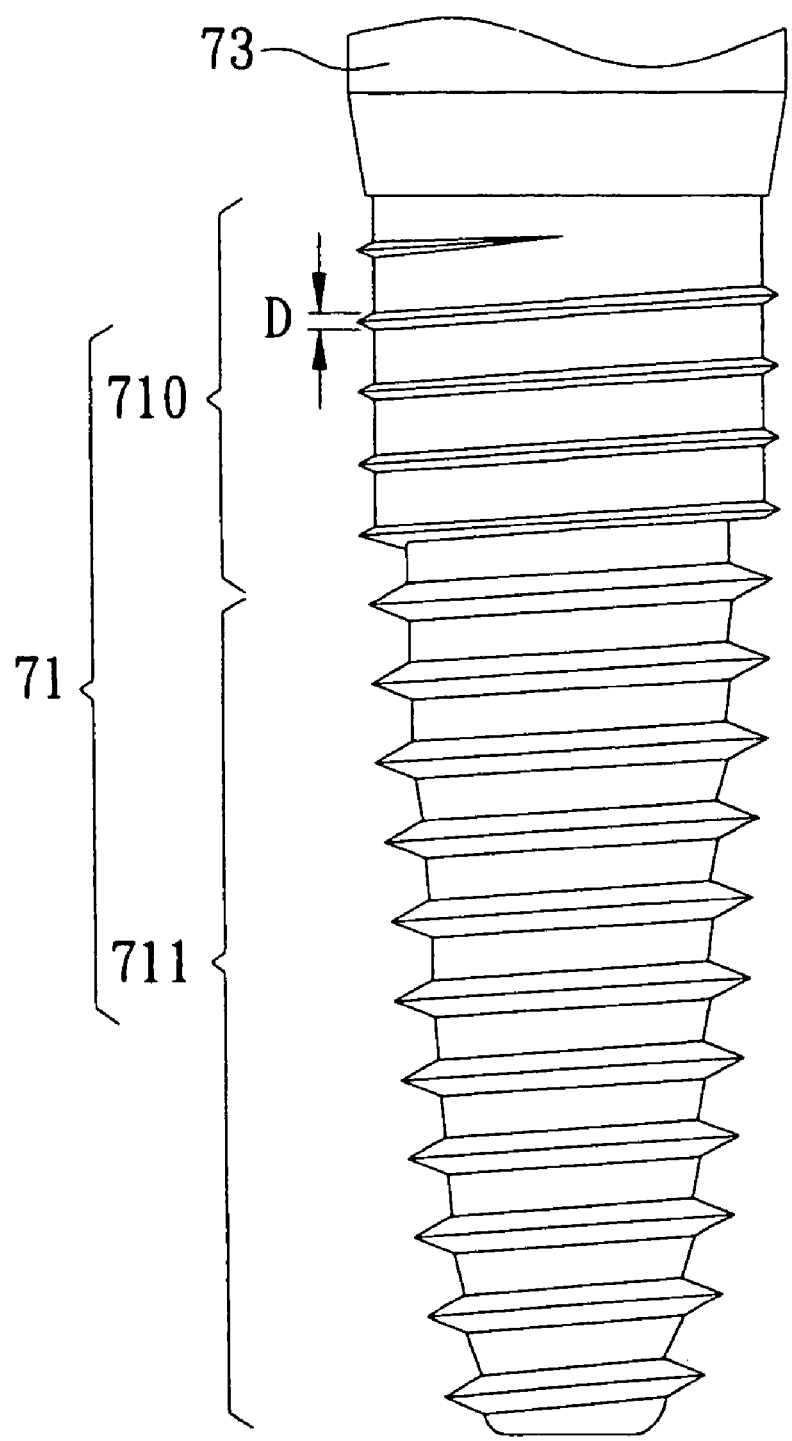
FIG. 9 is the sixth preferred embodiment of the screw-body part 71 of the screw device for orthodontic treatment of the present invention.

FIG. 9 is the sixth preferred embodiment of the screw-body part 71 of the screw device of the present invention. In this preferred embodiment, the threads of the screw-body part 71 can be divided into two or more groups, namely the first thread portion 710 which is located near to the platform part 73, and the second thread portion 711 located away from the platform part. The threads of the first thread portion 710 are designed to have relatively narrower width "D" and smaller pitch, while the threads of the second thread portion 711 have wider width and larger pitch. Typically, the width "D" of the threads of the first thread portion 710 can be between D=0.5~0.75 mm, while the width of the threads of the second thread portion 711 are larger than 0.75 mm. By applying such kind of configuration to the threads of the screw-body part 71, there will be more numbers of threads of the first thread portion 710 being engaged with the relatively firm outer structure of the maxilla/mandible of human being, so as to fix the screw-body part 71 into the maxilla/mandible tightly.

Figure 10:
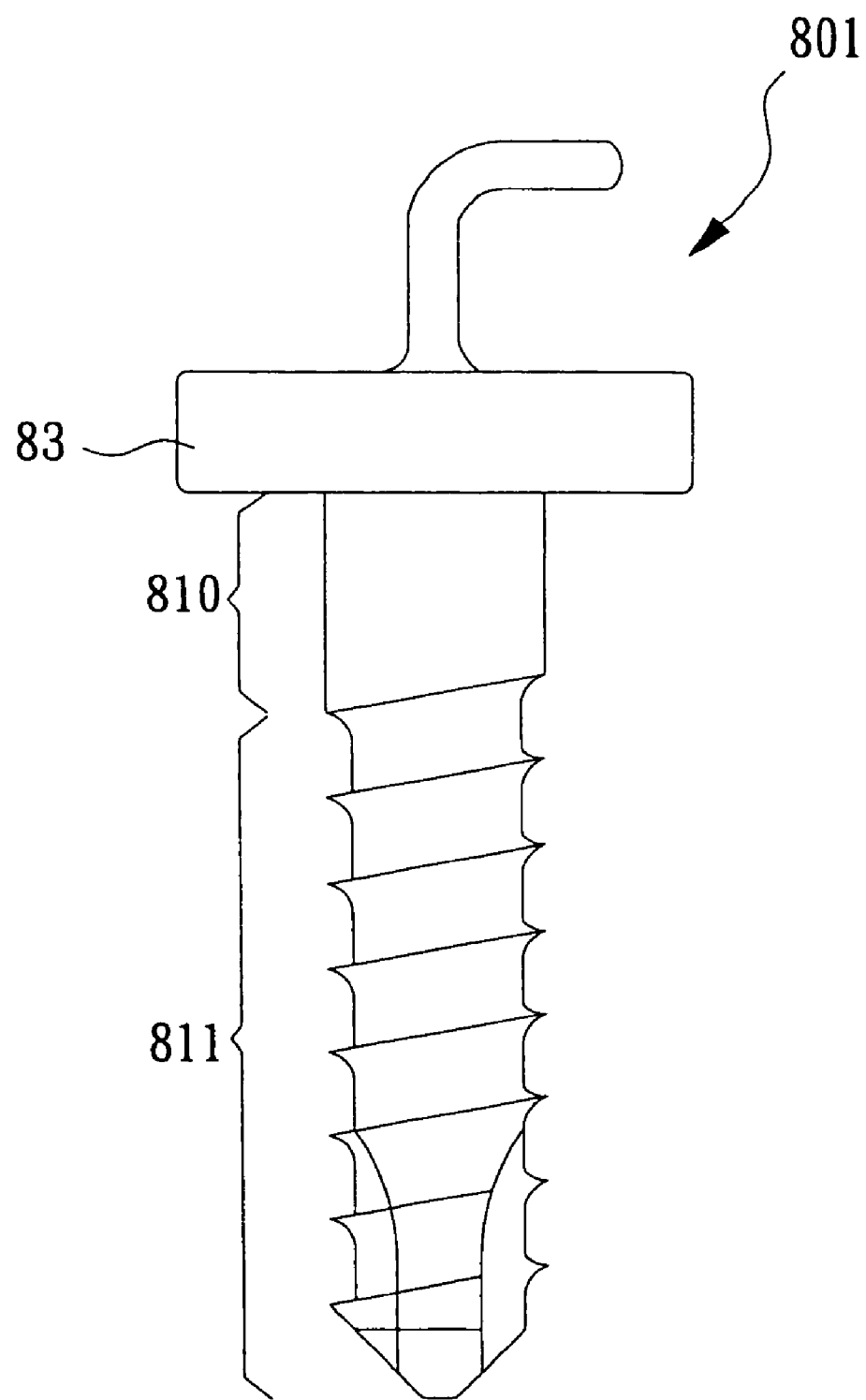
FIG. 10 is the seventh preferred embodiment of the screw device 80l of the present invention.

FIG. 10 is the seventh preferred embodiment of the screw device 801 of the present invention. In this preferred embodiment, the screw-body part includes a section 810 without any threads thereon at a location near to the platform part 83. Therefore, there exists a no-thread section 810 between the threads 811 and the platform part 83. The no-thread section 810 provides a smooth contact with the soft tissues located on the top surfaces of the maxilla/mandible after the screw device 801 is screwed into the maxilla/mandible. For some specific applications or some specific patients where/whose outer structures of the maxilla/mandible are fragile, the no-thread section 810 of the screw-body part can prevent the fragile structures of the maxilla/mandible being damaged by the threads.

Figure 11A:
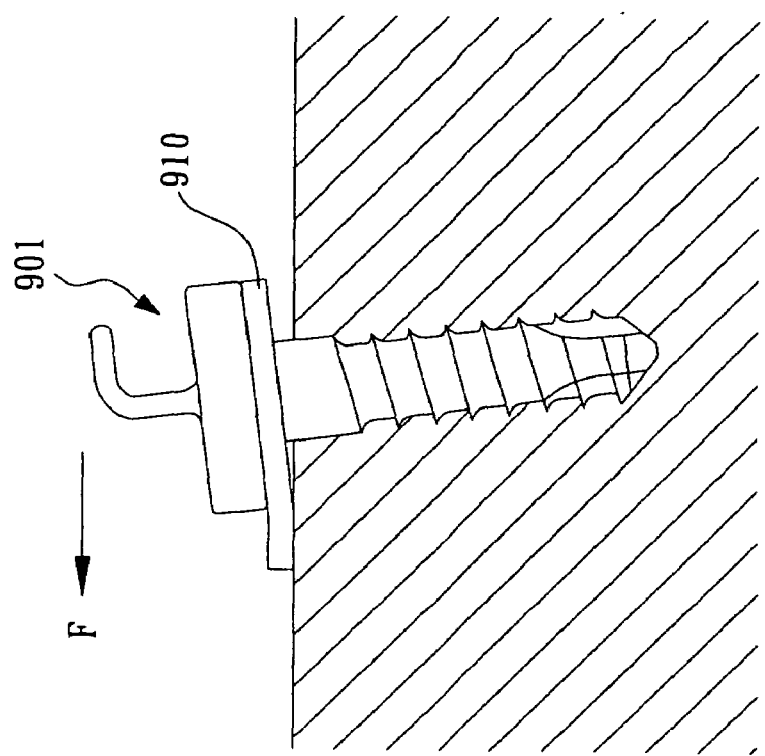
FIG. 11A and FIG. 11B are the eighth preferred embodiment of the screw device 90l of the present invention.
Figure 11B:
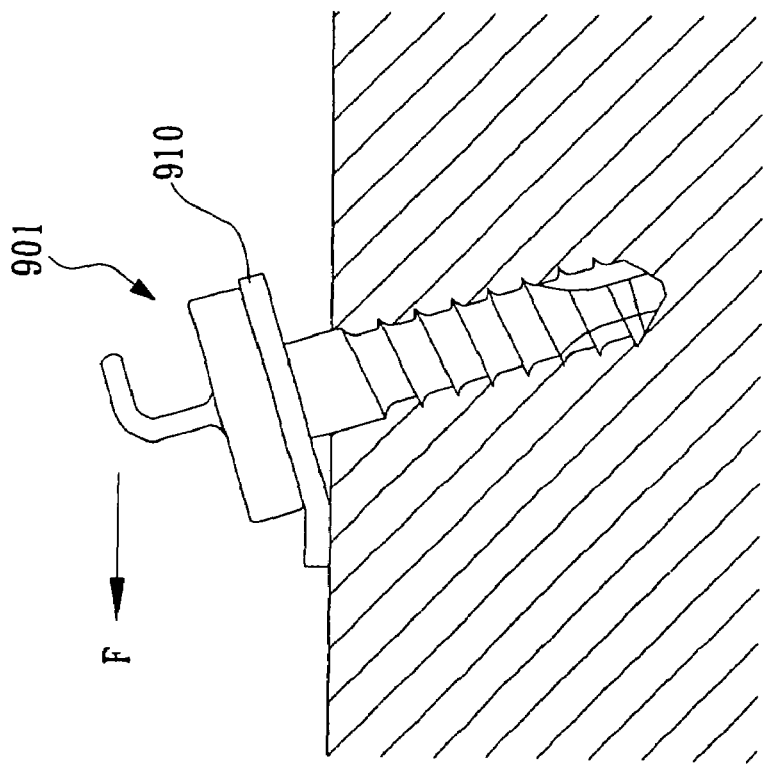

FIG. 11A and FIG. 11B are the eighth preferred embodiment of the screw device 901 of the present invention. In this preferred embodiment, an additional washer 910 is provided beneath the bottom surface of the platform part. The washer 910 is typically useful when the screw device 901 is crewed into the maxilla/mandible in an inclined angle. When the screw device 901 is screwed into the maxilla/mandible, the washer 910 is compressed, such that an internal force generated by the washer 910 will make the threads of the screw-body part of the screw device 901 to engage with the maxilla/mandible more firmly. The screw device 901 will not tend to loose even it is subject to a pulling force "F" resulted from an orthodontic spring (not shown in this figure).

Figure 12:
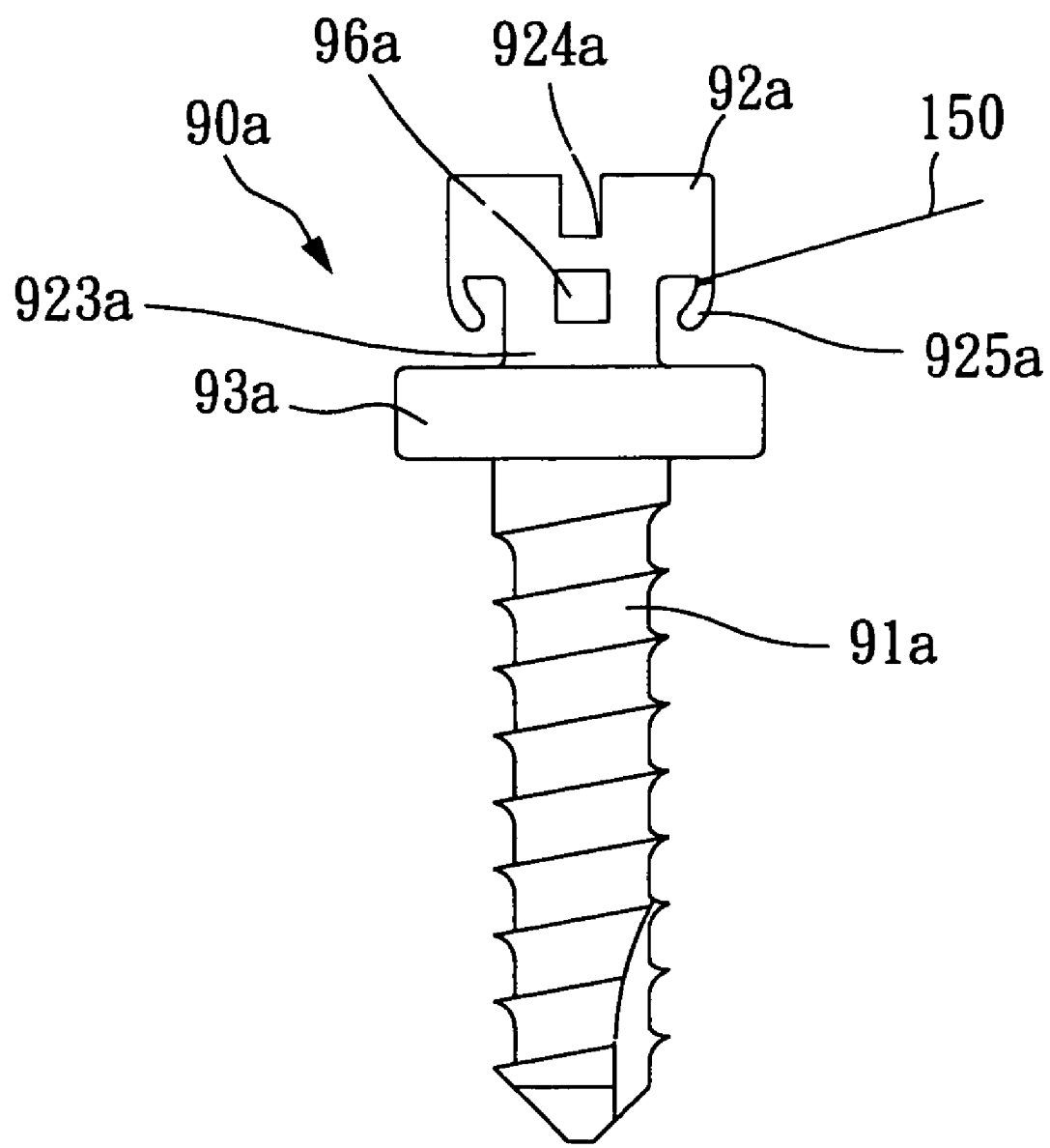
FIG. 12 is the ninth preferred embodiment of the screw device 90a of the present invention.

FIG. 12 is the ninth preferred embodiment of the screw device 90a of the present invention. The screw device 90a also comprises: a screw-body part 91a, a platform part 93a and a head part 92a. The screw-body part 91a, platform part 93a and head part 92a are integrally formed as a single element in this embodiment. A rectangular through hole 96a is formed at the neck portion 923a of the screw device 90a for allowing an orthodontic archwire to pass therethrough. The head part 92a is further formed with an orthodontic bracket 924a for accommodating an orthodontic archwire (not shown), a neck portion 923a for hooking an orthodontic spring (not shown), and a concave 925a extending downward from the bottom side of the orthodontic bracket 924a. The concave 925a allows the user to tie one end of stainless wires 150 or rubber bands onto the concave 925a, while to tie the other end of the stainless wires 150 or rubber bands onto the orthodontic archwire located on the orthodontic bracket 924a, so as to position the orthodontic archwire on the orthodontic bracket 924a firmly.

Figure 13:
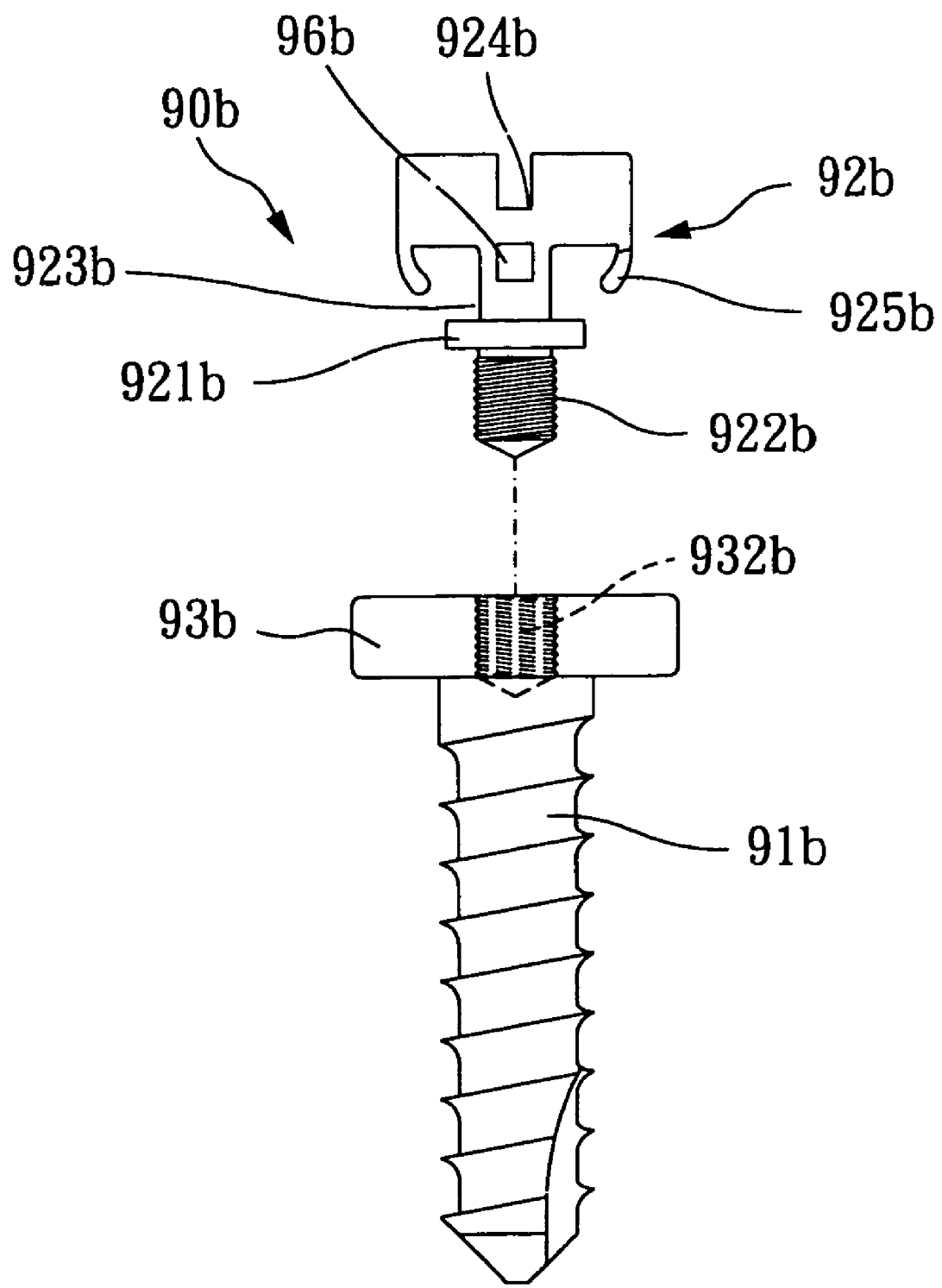
FIG. 13 is the tenth preferred embodiment of the screw device 90b of the present invention.

FIG. 13 is the tenth preferred embodiment of the screw device 90b of the present invention. The screw device 90b comprises: a screw-body part 91b, a platform part 93b and a head part 92b. In this preferred embodiment, the head part 92b is an independent component and is detachable from the platform part 93b of the screw device 90b. The head part 92b is further formed with a flat cap 921b, a second mating structure 922b, a neck portion 923b, an orthodontic bracket 924b, and a concave 925b. The platform part 93b is further formed with a first mating structure 932b for engaging with the second mating structure 922b. A rectangular through hole 96b is formed in the neck portion 923b of the screw device 90b for allowing an orthodontic archwire to pass therethrough.

Figure 14B:
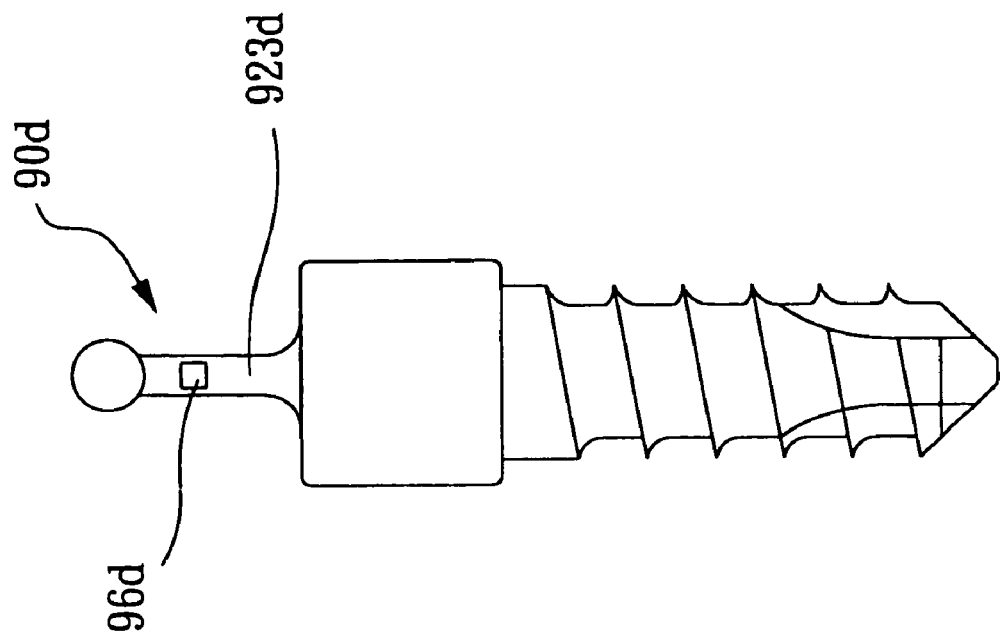
FIG. 14B is the twelfth preferred embodiment of the screw device 90d of the present invention.
Figure 14A:
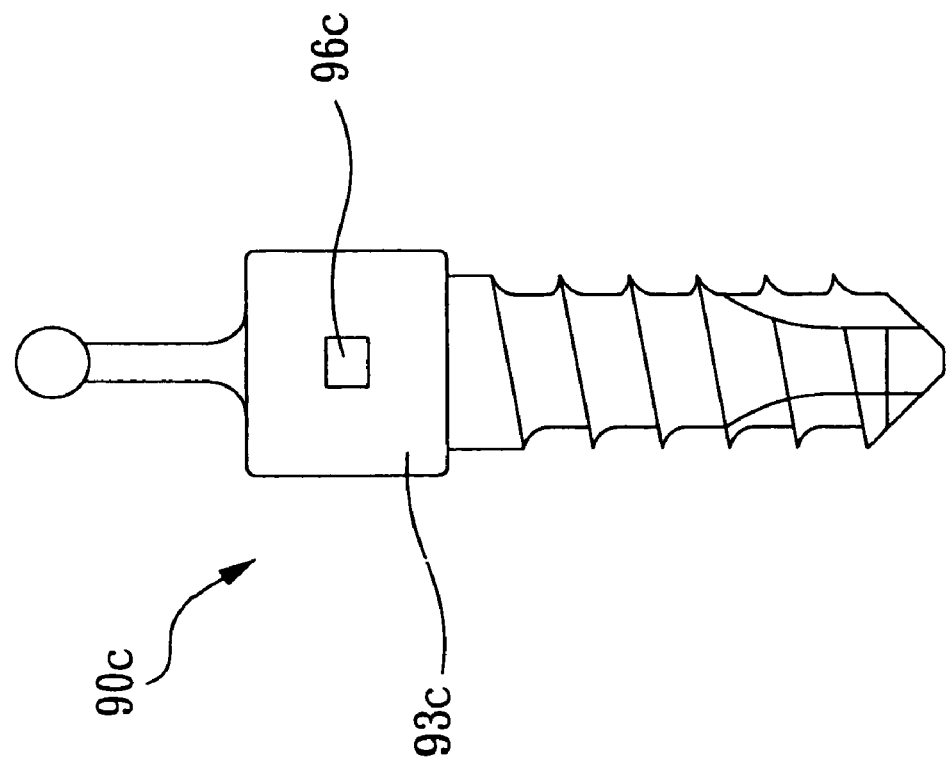
FIG. 14A is the eleventh preferred embodiment of the screw device 90c of the present invention.

FIG. 14A and FIG. 14B are the eleventh and the twelfth preferred embodiments of the screw devices 90c, 90d of the present invention. In the preferred embodiment shown in FIG. 14A, a rectangular through hole 96c is further formed in the platform part 93c of the screw device 90c for allowing an orthodontic archwire to pass therethrough. In FIG. 14B, a rectangular through hole 96d is formed in the neck portion 923d of the screw device 90d for allowing an orthodontic archwire to pass therethrough. The screw devices 90c, 90d can either be integrally formed, or have detachable head parts as previously described.

Figure 15:
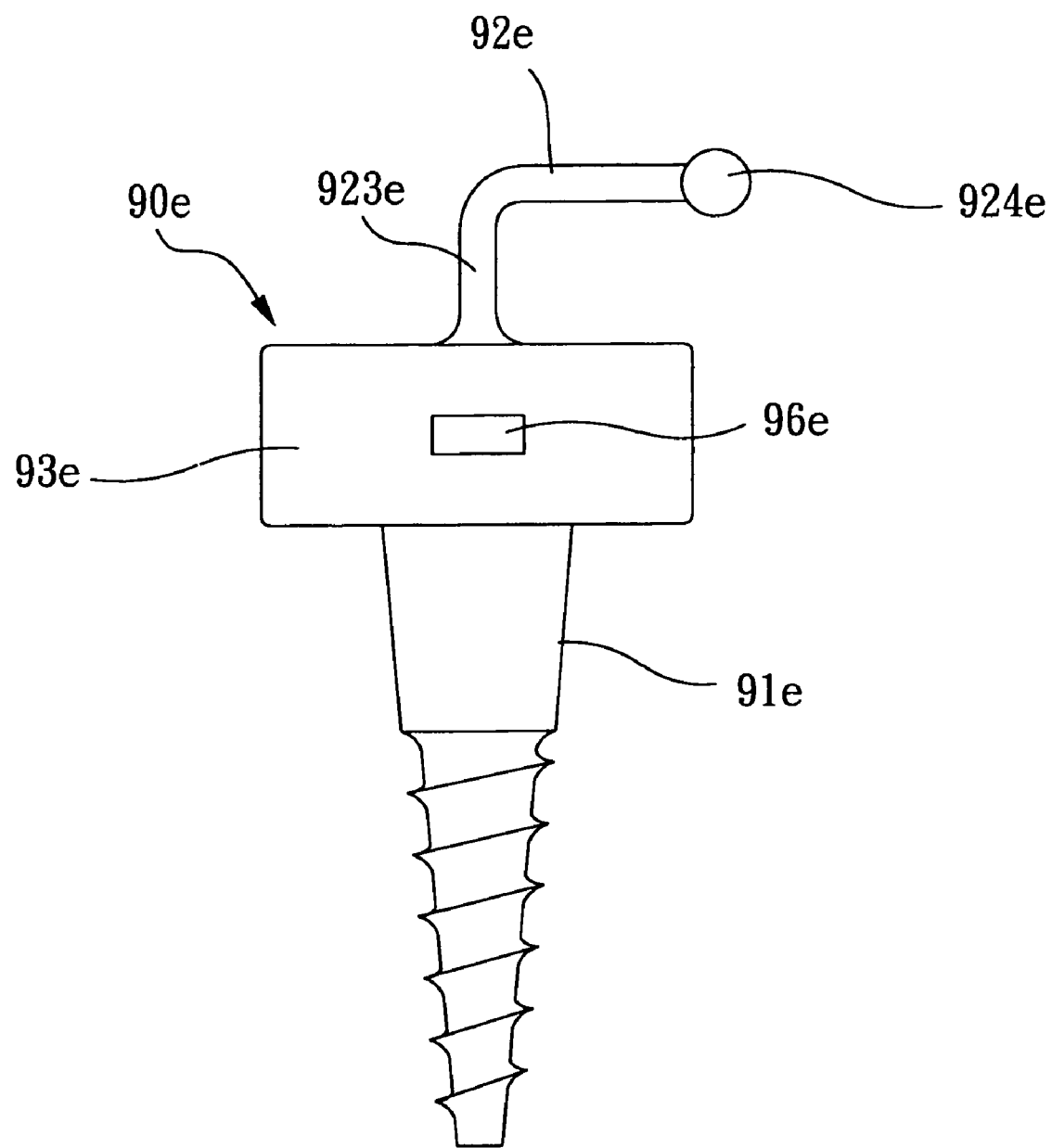
FIG. 15 is the thirteenth preferred embodiment of the screw device 90d of the present invention.

FIG. 15 is the thirteenth preferred embodiment of the screw device 90e of the present invention. The screw device 90e comprises: a screw-body part 91e, a platform part 93e and a head part 92e. The head part 92e has a neck portion 923e which is bended as a L-shaped structure. A ball head 924e having a diameter greater than the neck portion is formed on the free end of the neck portion 923e such that the orthodontic spring will not drop off when it is hooked on the neck portion 923e. The screw-body part 91e is tapered and includes a no-thread section near to the platform part 93e. A rectangular through hole 96e is formed in the platform part 93e for allowing an orthodontic archwire to pass therethrough.

Although the present invention has been described with reference to a preferred embodiment, it should be appreciated that various modifications and adaptations can be made without departing from the scope of the invention as defined in the claims.

What is claimed is:

1. A screw device for orthodontic treatment comprising:
   a screw-body part having a diameter with external threads extending a length;
   a platform part axially aligned and integrally formed with the screw-body part, the platform part further having:
      a flat top plane perpendicular to the screw-body part; and
      an outer periphery being a smooth surface without threads thereon; and
   a head part connected on the flat top plane of the platform part wherein the head part is detachable from the platform part and further includes an accessory member for assisting orthodontic treatment, the accessory member comprising a cube having a plurality of flat side surfaces adapted for adhering an additional component to one of the flat side surfaces to assist orthodontic treatment; and
   threads of the screw-body part are divided into at least a first thread portion located near to the platform part and a second thread portion located away from the platform part, wherein the threads of the first thread portion are designed to have relatively narrower width and smaller pitch, while the threads of the second thread portion have wider width and larger pitch.

2. The screw device for orthodontic treatment according to claim 1, wherein the screw-body part is tapered at a section away from the platform part, and said tapered section of the screw-body part has a tapering angle of 2~10 degrees.

3. The screw device for orthodontic treatment according to claim 1, wherein the screw-body part includes a section without any threads thereon at a location near to the platform part.

4. The screw device for orthodontic treatment according to claim 1, further comprising an additional washer which is provided beneath a bottom surface of the platform part.

5. The screw device for orthodontic treatment according to claim 1, wherein the platform part forms a rectangular through hole.

6. The screw device for orthodontic treatment according to claim 1, wherein the screw-body part is tapered and includes a no-thread section located adjacent to the platform part, and the platform Dart has a rectangular through hole for allowing an orthodontic archwire to pass therethrough.

7. A screw device for orthodontic treatment comprising:
a screw-body part having a diameter with external threads extending a length wherein the threads are divided into at least a first thread portion located near to a platform part and a second thread portion located away from the platform part, wherein the threads of the first thread portion are designed to have relatively narrower width and smaller pitch, while the threads of the second thread portion have wider width and larger pitch;
the platform part axially aligned and integrally formed with the screw-body part, wherein the platform part comprises:
a flat top plane perpendicular to the screw-body part; and
an outer periphery being a smooth surface without threads thereon; and
a head part connected on the flat top plane of the platform part wherein the head part is detachable from the platform part and further includes a flat cap and an accessory member formed on the flat cap, wherein the accessory member has an inclined plane located on the flat cap and the inclined plane has an inclined angle relative to an axial direction of the screw-body part adapted for adhering an additional component to the inclined plane for assisting orthodontic treatment.

8. A screw device for orthodontic treatment comprising:
a screw-body part having a diameter with external threads extending a length;
a platform part axially aligned and integrally formed with the screw-body part, the platform part further having:
a flat top plane perpendicular to the screw-body part; and
an outer periphery being a smooth surface without threads thereon; and
a head part connected on the flat top plane of the platform part and comprising a neck portion having a diameter smaller than the platform part; wherein the head part forms an orthodontic bracket for accommodating a first orthodontic archwire and a concave which is downward from a bottom side of the orthodontic bracket, and the neck portion of the head part forms a rectangular through hole allowing a second orthodontic archwire to pass therethrough.

9. The screw device for orthodontic treatment according to claim 8, wherein the head part is detachable from the platform part.

10. The screw device for orthodontic treatment according to claim 9, wherein the threads of the screw-body part are divided into at least a first thread portion located near to the platform part and a second thread portion located away from the platform part, the threads of the first thread portion are designed to have relatively narrower width and smaller pitch, while the threads of the second thread portion have wider width and larger pitch.

* * * * *